United States Patent [19]

Lundquist

[11] Patent Number: 4,642,098

[45] Date of Patent: Feb. 10, 1987

[54] IV SYSTEM AND CONTROLLER AND COMBINATION IV FILTER AND PUMP ASSEMBLY FOR USE THEREIN AND METHOD

[75] Inventor: Ingemar Lundquist, Oakland, Calif.

[73] Assignee: Valleylab, Inc., Boulder, Colo.

[21] Appl. No.: 725,657

[22] Filed: Apr. 22, 1985

Related U.S. Application Data

[63] Continuation-in-part of Ser. No. 278,635, Jun. 29, 1981.

[51] Int. Cl.$^4$ ............................................. A61M 5/00
[52] U.S. Cl. ...................... 604/123; 604/126; 604/152; 128/DIG. 12; 417/388
[58] Field of Search ................ 604/122, 123, 126, 67, 604/151, 152, 153; 128/DIG. 12, DIG. 13; 417/383–388, 395, 479

[56] References Cited

U.S. PATENT DOCUMENTS

| | | | |
|---|---|---|---|
| 3,457,909 | 7/1969 | Laird | 604/67 X |
| 3,961,860 | 6/1976 | Ernst | 417/388 X |
| 4,030,495 | 6/1977 | Virag | 604/126 X |
| 4,142,524 | 3/1979 | Jassawalla et al. | 604/123 |
| 4,261,360 | 4/1981 | Perez | 604/31 |
| 4,262,668 | 4/1981 | Schmidt | 604/126 |
| 4,316,460 | 2/1982 | Genese et al. | 604/126 X |

*Primary Examiner*—Stephen C. Pellegrino
*Attorney, Agent, or Firm*—Flehr, Hohbach, Test, Albritton & Herbert

[57] ABSTRACT

An IV filter and pump assembly having first and second bodies secured into a unitary assembly. The first and second bodies provide a chamber. One of the bodies has an opening therein in communication with said chamber and an inlet port therein. The other of the bodies has an outport therein. The inlet and outlet ports are in communication with the chamber. An inlet valve controls the flow of liquid through the inlet port and an outlet valve controls the flow of liquid through the outlet port. A hydrophobic filter is carried by the unitary assembly and is in communication with the upper portion of said chamber for venting to ambient small quantities of air in said chamber. An actuator supplies a pumping action to the liquid in the chamber so that liquid is caused to be moved out of the chamber through the outlet valve and into the chamber through the inlet valve.

17 Claims, 24 Drawing Figures

FIG. —7

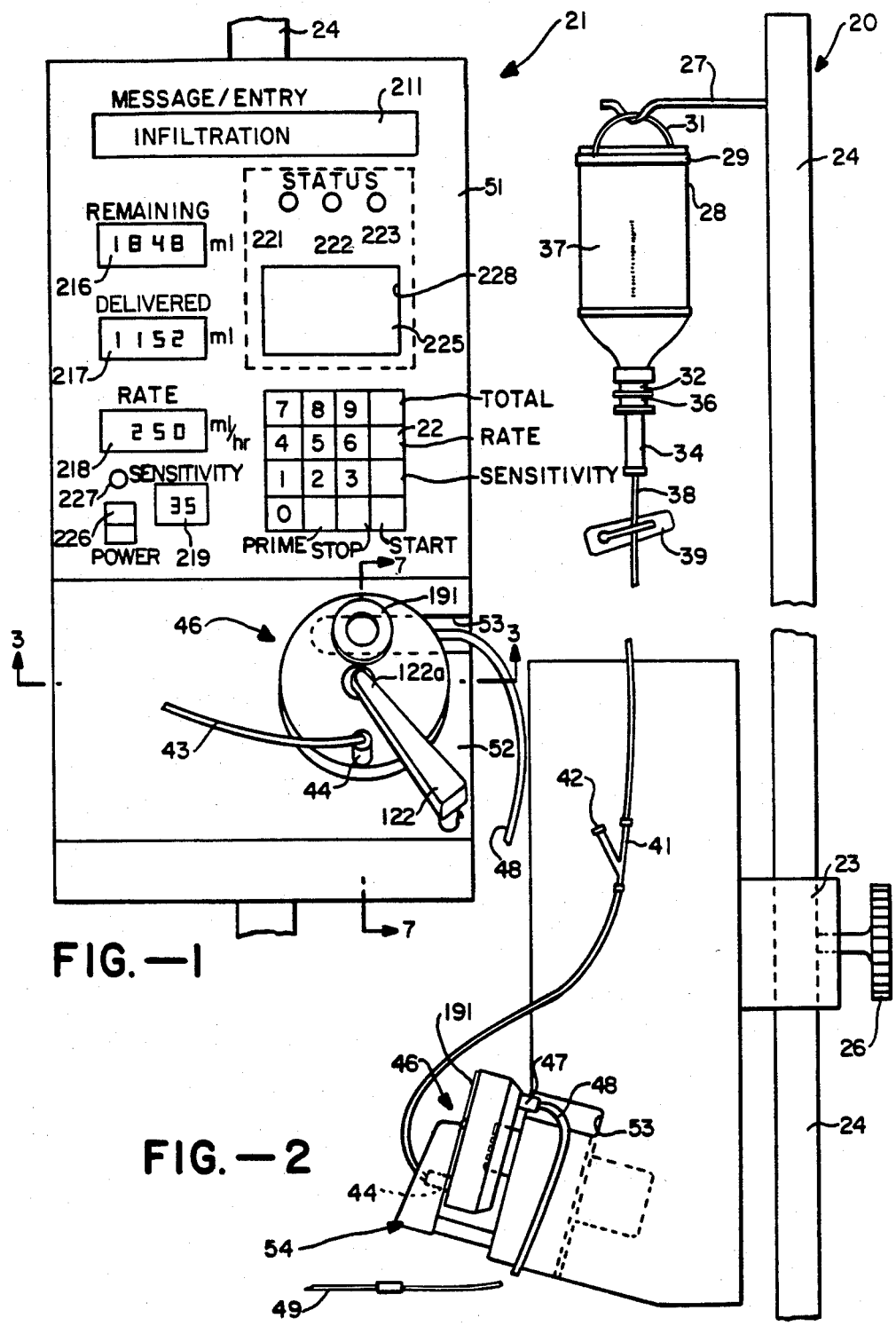

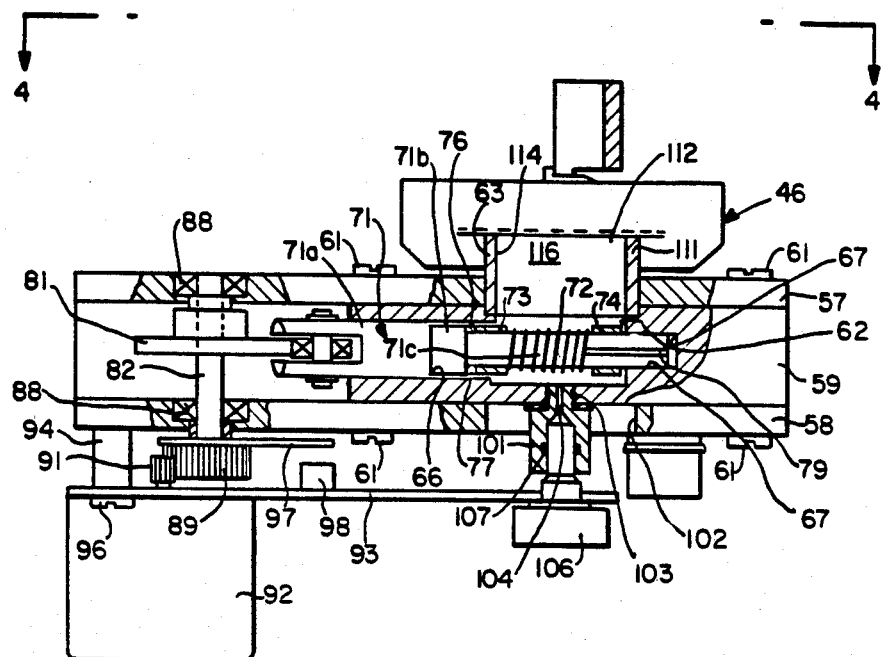
FIG.—3
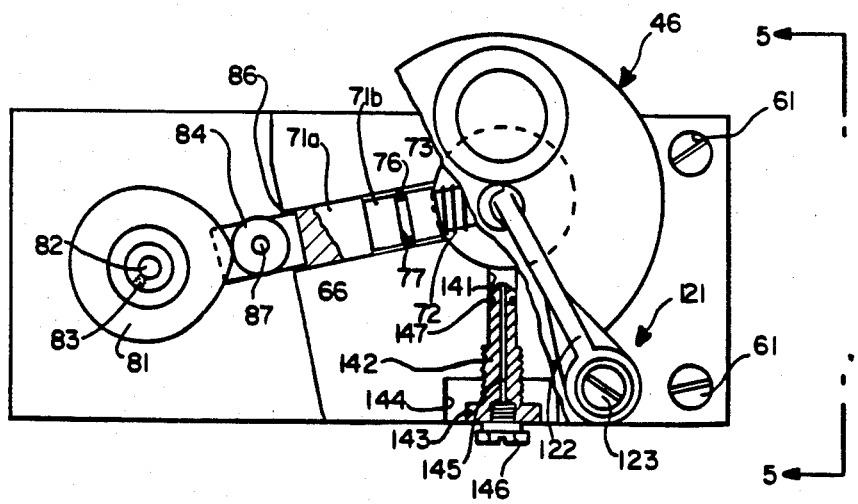
FIG.—4

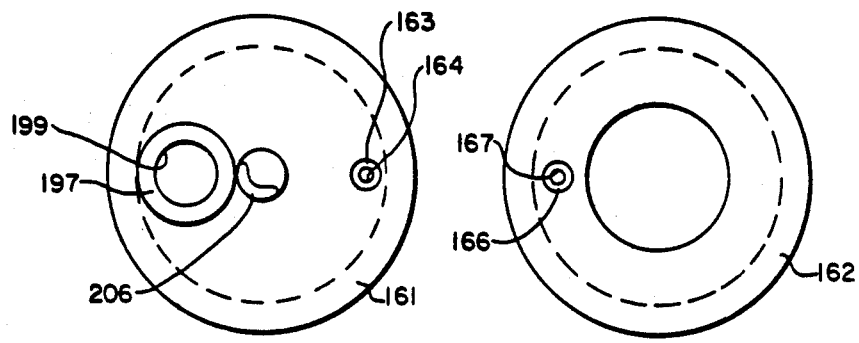
FIG.—8    FIG.—9
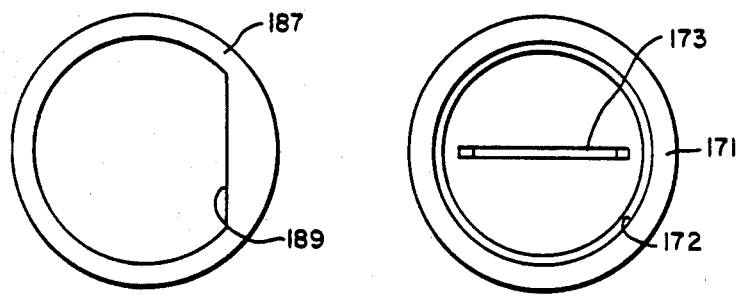
FIG.—10    FIG.—11
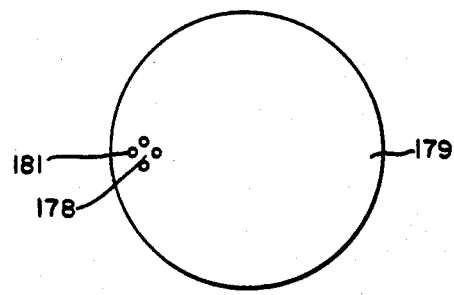
FIG.—12

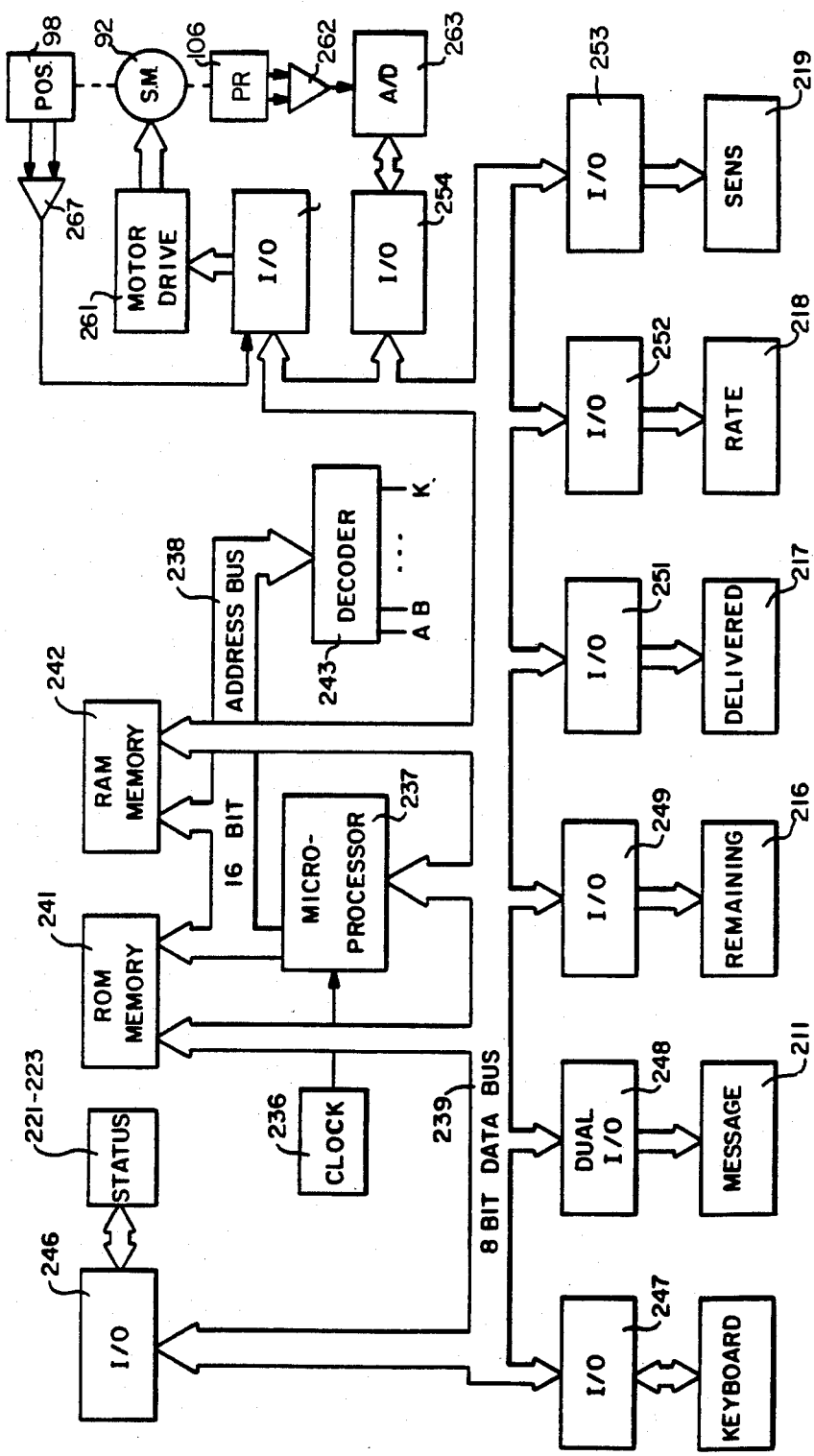
FIG.—13

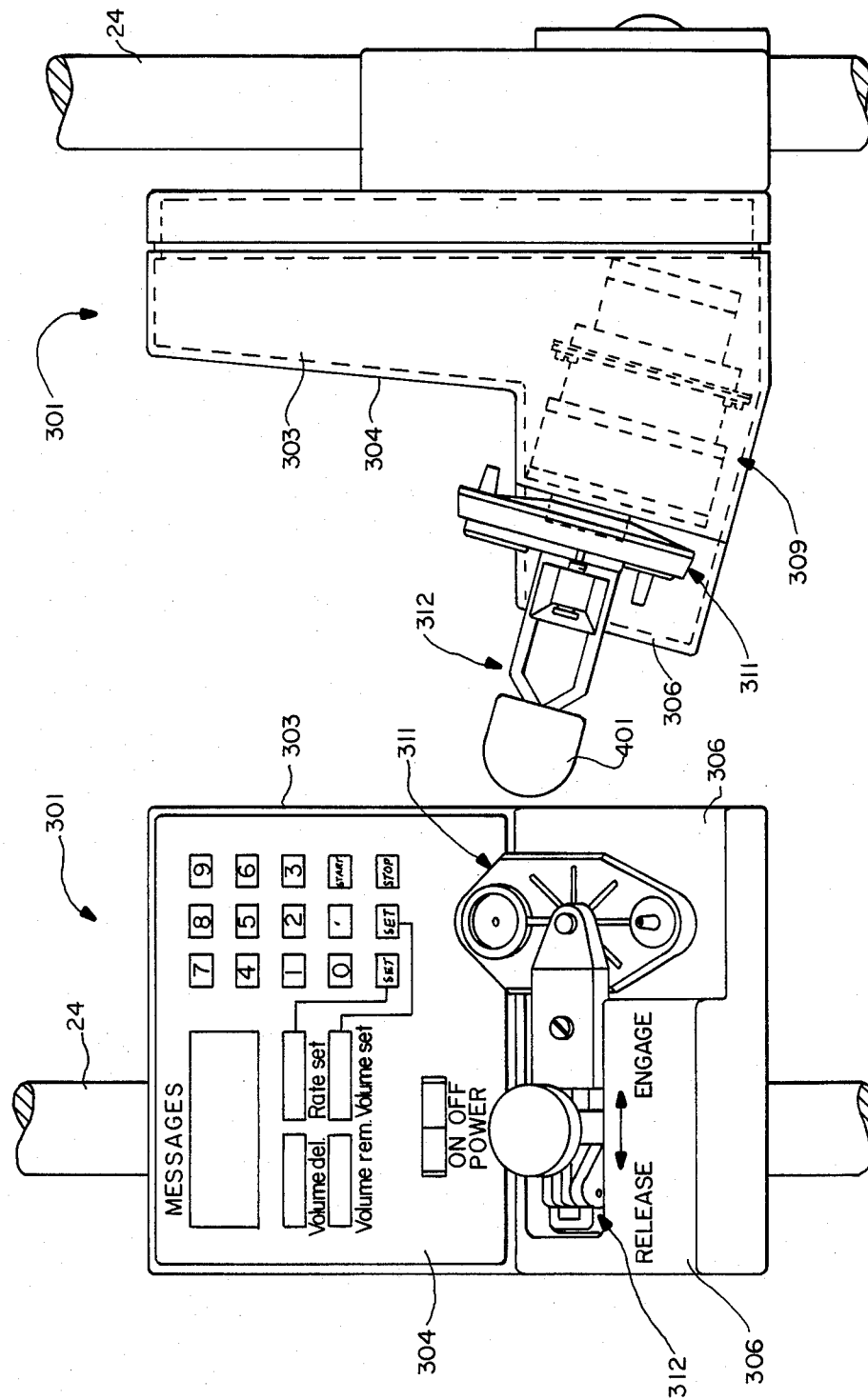

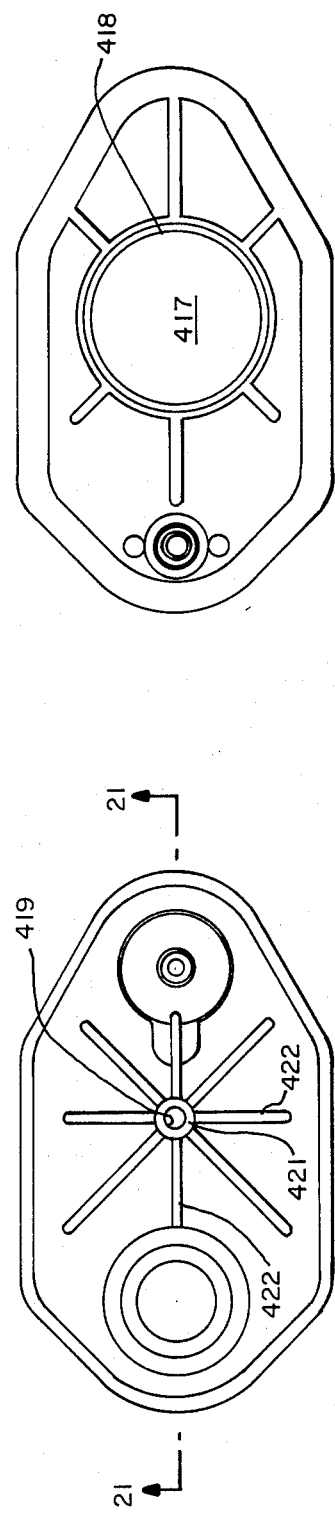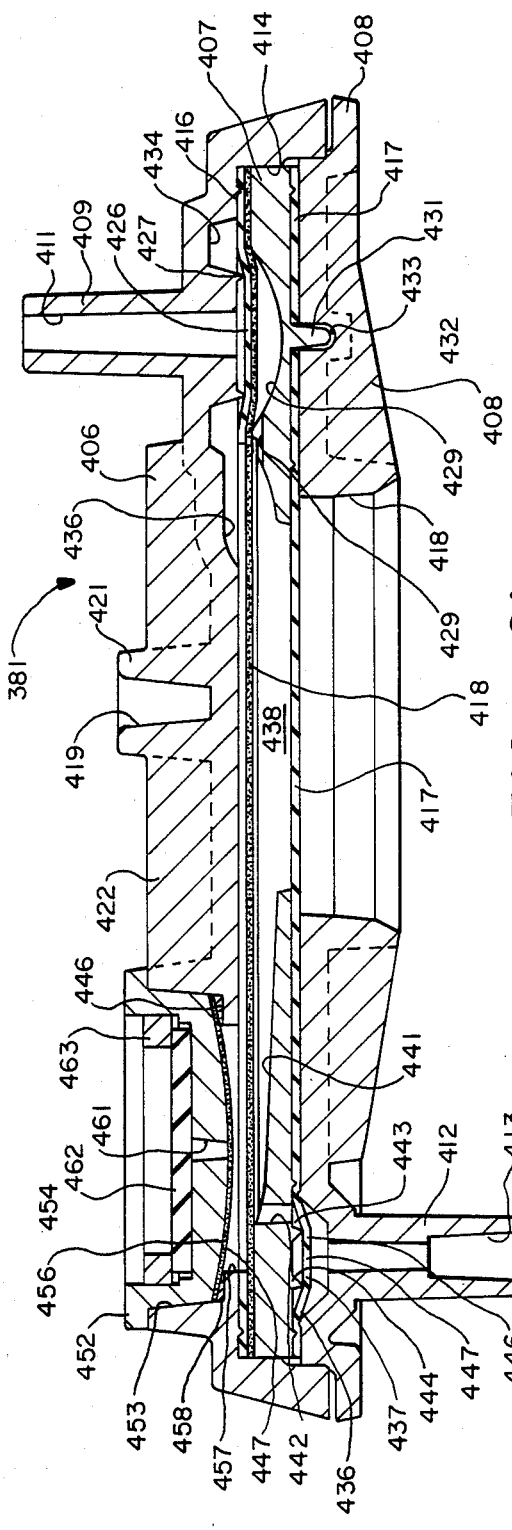

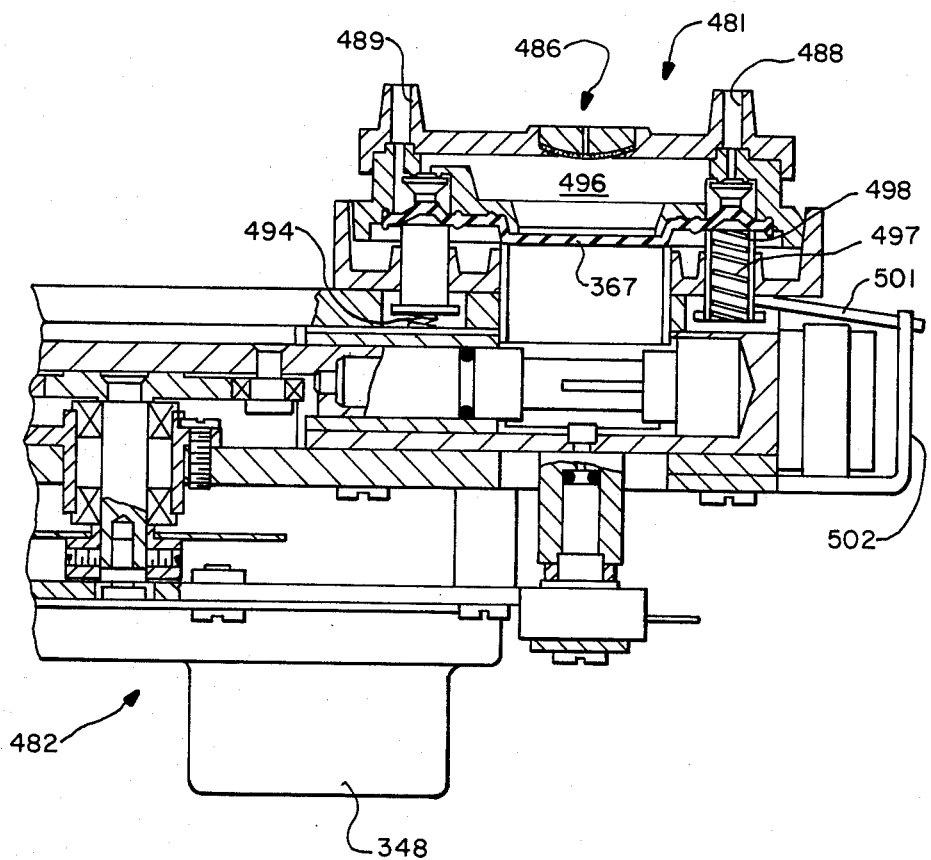
FIG.—22

IV SYSTEM AND CONTROLLER AND COMBINATION IV FILTER AND PUMP ASSEMBLY FOR USE THEREIN AND METHOD

This application is a continuation-in-part of application Ser. No. 278,635 filed on June 29, 1981 now abandoned.

This invention relates to an IV system and controller and combination intravenous filter and pump assembly for use therein and method.

Heretofore, various types of IV pumps have been provided. In the past, such pumps in and of themselves did not have a capability of filtering out bacteria. Typically, filters for this purpose have been added at the distal end of a tube leading from the outlet of the pump. In addition, in available pumps, there has been considerable difficulty in eliminating air. Also, in conventional pumps it has been difficult to provide alarms for different types of pump failure. Controllers have also been provided heretofore for operating the IV pumps. In the past, the controllers for such pumps have had limited features for controlling operations of the pump and for giving the necessary information on the operation of the pumps. There is therefore a need for a new and improved pump and more particularly, a combined filter and pump assembly as well as a controller and system for operating the same.

In general, it is an object of the present invention to provide an IV system and controller and combination IV filter and pump assembly for use therewith, and method in which pressure is sensed at all times. Another object of the present invention is to provide a system, controller, assembly and method of the above character in which pressure sensing is used for sensing underpressures and overpressures.

Another object of the invention is to provide a combination IV filter and pump assembly in which filtering is provided in the pump itself for filtering out bacteria prior to at least the last pressure valve in the pump assembly.

Another object of the invention is to provide a combination filter and pump assembly of the above character in which a hydrophilic filter is utilized for filtering out the bacteria.

Another object of the invention is to provide a filter and pump assembly of the above character in which a hydrophobic filter is provided for permitting air entering into the filter and pump assembly to be vented to the atmosphere.

Another object of the invention is to provide a filter and pump assembly of the above character in which the need for a separate filter distal to the pump assembly is eliminated.

Another object of the invention is to provide a filter and pump assembly of the above character having rubber parts which are flat parts that are easy to manufacture by conventional die stamping.

Another object of the invention is to provide a filter and pump assembly of the above character in which the presence of air can be readily sensed.

Another object of the invention is to provide a filter and pump assembly of the above character in which air cannot reach the patient through the assembly.

Another object of the invention is to provide a filter and pump assembly of the above character in which particulates in the IV fluid cannot reach the patient.

Another object of the invention is to provide a filter and pump assembly of the above character which has a very small fill volume.

Another object of the invention is to provide a filter and pump assembly of the above character which is not of a flow through type.

Another object of the invention is to provide a filter and pump assembly of the above character which particularly lends itself to being formed into disposable cassettes.

Another object of the invention is to provide a controller for use in driving the combination filter and pump assembly which is provided with large bearing surfaces to provide long wear and great accuracy.

Another object of the invention is to provide a controller of the above character in which the operation of the combined filter and pump assembly is such that liquid is supplied to the patient for a relatively long period of time in comparison to the time in which liquid is not being introduced into the patient.

Another object of the invention is to provide a controller of the above character in which a microprocessor is utilized for programming the same.

Another object of the invention is to provide a controller of the above character in which the sensitivity to pressure changes can be varied.

Another object of the invention is to provide a system of the above character in which appropriate alarms can be initiated.

Another object of the invention is to provide a system of the above character in which the microprocessor performs self-testing.

Another object of the invention is to provide a system of the above character in which many safety features have been provided.

Another object of the invention is to provide a pump assembly of the above character in which the piston is positively driven in both directions.

Another object of the invention is to provide a pump assembly of the above character in which the improved cassette is provided.

Another object of the invention is to provide a pump assembly of the above character in which the cassette is readily manufacturable.

Another object of the invention is to provide a pump assembly of the above character in which the cassette provides improved control over the opening and closing pressures.

Another object of the invention is to provide a pump assembly of the above character in which an improved hydrophobic filter is utilized.

Another object of the invention is to provide a pump assembly of the above character having a cassette which is self venting.

Another object of the invention is to provide a pump assembly of the above character in which the cassette can be vented while it is mounted on the pump assembly.

Another object of the invention is to provide a pump apparatus of the above character in which air will not collect within the cassette.

Additional objects and features of the invention will appear from the following description in which the preferred embodiments are set forth in detail in connection with the accompanying drawings.

FIG. 1 shows an IV administration system and in particular a front elevational view of a controller with a combination filter and pump assembly mounted therein utilized in a system of the present invention.

FIG. 2 is a side elevational view of the system shown in FIG. 1.

FIG. 3 is a cross-sectional view taken along the line 3—3 of FIG. 1.

FIG. 4 is a cross-sectional view looking along the line 4—4 FIG. 3.

FIG. 8 is a view looking along the line 8—8 of FIG. 7.

FIG. 9 is a view looking along the line 9—9 of FIG. 7.

FIG. 10 is the top plan view of the upper gasket utilized in the combination filter and pump assembly.

FIG. 11 is a plan view of the filter support plate forming a part of the combination filter and pump assembly.

FIG. 12 is a plan view of the outlet valve member of the combination filter and pump assembly.

FIG. 13 is a schematic diagram of the electrical circuitry utilized in the controller.

FIG. 15 is a front elevational view of a controller with a combination filter and pump assembly mounted therein incorporating another embodiment of the present invention and utilized in the system of the present invention.

FIG. 16 is a side elevational view of the controller shown in FIG. 15.

FIG. 19 is a top plan view of the cassette shown in FIGS. 14 and 15.

FIG. 20 is a bottom plan view of the cassette shown in FIG. 19.

FIG. 21 is a cross-sectional view taken along the line 21—21 of FIG. 19.

FIG. 22 is a cross-sectional view of another embodiment of the invention showing a modified cassette used with a drive module of the type shown in FIG. 17.

Figure 5:
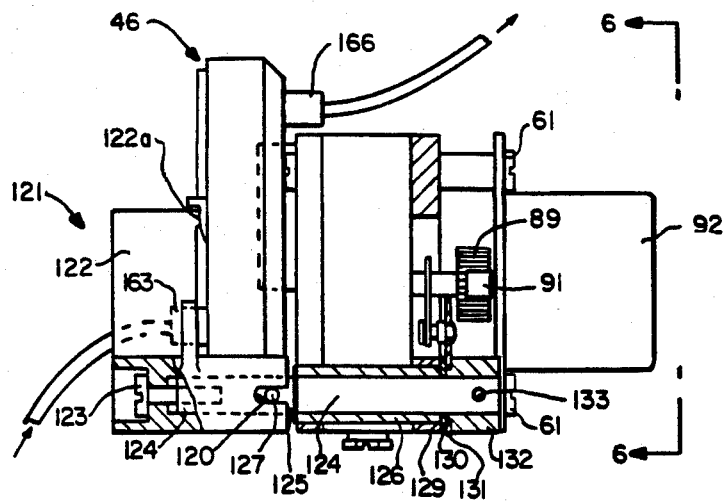
FIG. 5 is an elevational view looking along the line 5—5 of FIG. 4.
Figure 6:
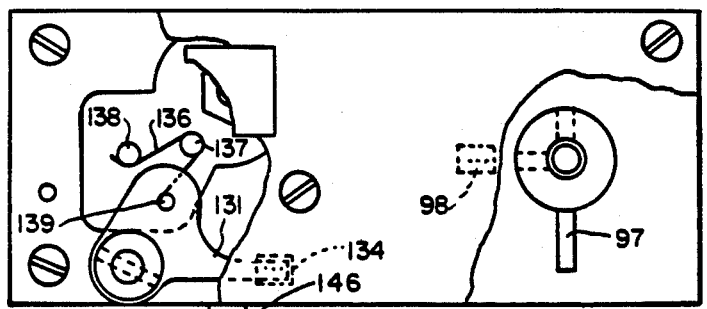
FIG. 6 is a rear elevational view looking along the line 6—6 of FIG. 5.

The combination IV filter and pump assembly consists of a pump body having first and second parts. Means is provided for securing the first and second parts into a unitary assembly to form the pump body with a liquid-tight chamber therein.

A hydrophilic filter is disposed in the chamber and divides the chamber into first and second regions. Inlet valve means is carried by the first part and opens into the first region. Outlet valve means is carried by the second part and opens into the second region, the outlet valve means being offset from the set valve means in a vertical direction when the assembly is in use. Hydrophobic filter means is carried by the first part and is in communication with the first region to permit air entering through the inlet valve means to be vented to ambient.

As shown in FIGS. 1 and 2, the IV system 20 of the present invention consists of a controller 21. The controller includes a cabinet 22 having a manually adjustable clamp 23 secured to the rear wall thereof which is adapted to be utilized to secure the controller to a suitable support such as the pole 24 mounted upon a stand (not shown). The clamp 23 is provided with the knob 26 for adjusting the frictional engagement between the clamp 23 and the pole 24. The pole 24 carries a hanger 27 on which there is suspended a suitable source of IV fluid such as a bottle 28 which is provided with a ring 29 surrounding the same and which has attached thereto support handle 31 adapted to be carried by the hanger 27. Such a bottle is typically provided with a stopper 32. A drip member 34 which is provided with a hollow needle 36 extends through the stopper 32 so that it can receive IV liquid 37 from the bottle 28. The drip chamber 34 is connected to a flexible tube 38 which carries a conventional on/off clamp 38 and which is connected to a wye 41 that provides an injection site 42. The wye 42 is connected to another length of tube 43 which is connected to an inlet fitting 44 of the combination filter and pump assembly 46 incorporating the present invention. The filter and pump assembly 46 is provided with an outlet fitting 47 which is connected to a tube 48. The tube 48 is connected to a needle adapter 49 of a type which is adapted to be introduced into the vein of a patient.

The controller 21 is provided with an upper front panel 51 which is provided with a plurality of controls and displays of a type hereinafter described. It also includes a lower front panel 52 which is provided with a generally U-shaped slot 53 extending horizontally of the panel near the upper extremity of the panel. The slot 53 is provided for receiving the combination filter and pump assembly 46 as hereinafter described. The manually operable clamp assembly 54 is secured to the lower front panel 52 and is adapted to engage the filter and pump assembly 46 and to retain the same in place of the lower front panel 52. As can be seen from FIG. 2, the lower front panel 52 is included at an angle. The bottom extremity of the panel 52 extends forwardly with respect ot the vertical upper front panel 51.

The controller 21 includes a mechanical drive assembly 56 consisting of first and second spaced parallel plates 57 and 58 formed of a suitable material such as brass and which have mounted therebetween a block or a body 59 which also can be formed of a suitable material such as brass. The plates 57 and 58 and the block 59 are fastened together by screws 61. The body 59 is provided with a large cylindrical recess 62 which opens through one side of the body 59 and which is in registration with a cylindrical bore 63 provided in the side wall 57 and having an axis which extends perpendicular to the plane of the side wall 57. A large bore 66 is provided in the body 59 and extends in a direction which is parallel to the planes of the walls 57 and 58 and is inclined upwardly in a forwardly direction as viewed in FIG. 4. The bore 66 opens into the recess 62 at right angles to the axis of the recess 62. Another smaller cylindrical bore 67 is provided in the body 59 and opens into the recess 62 also in a direction at right angles to the axis of the recess 62 and is in axial alignment with the bore 66. As can be seen, bores 66 and 67 are diametrically disposed with respect to the recess 62.

A piston assembly 69 is mounted in the bores and 67. The piston assembly 69 consists of a piston member 71 which is provided with a cylindrical portion 71a that forms a relatively tight friction fit with the bore 66. It also is provided with a portion 71b which is slightly smaller diameter than portion 71a. It is also provided with a portion 71c which forms a relatively tight friction fit with the smaller bore 67. From this construction it can be seen that the travel of the piston member 1 is guided on its forward and rear extremities. A helical return spring 72 is coaxially mounted upon the piston member 71 intermediate the ends of the same and engages sleeves 73 and 74 which are slidably mounted on the piston member 71. The sleeve 73 rests against an O-ring 76 carried by the piston member 71 and the O-ring 76 engages a shoulder 77 formed on the piston member 71. The other sleeve 74 rests against the inner surface forming the recess 62. The piston member 71 is provided with a pair of diametrically opposed slots 79 opening through the side surface forming the portion 71c of the piston member 71 and extend from the forwardmost end of the piston member 71 into a region which extends into the recess 62. The recessed area 71b is provided so that it will travel along the surface which is engaged by the O-ring 76. This ensures that there will be no scratching of the surface which is engaged by the portions 71a and 71c of the piston-like member 71. In order for a liquid-tight seal to be formed between the piston member 71 and the piston block or body 59, a mirror-type polish is provided on the piston member and in the bores 66 and 67 so as to provide long-wearing precision surfaces.

Means is provided for moving the piston member 71 forwardly against the force of the return spring 72 and consists of a cam member 81 which is secured to a shaft 82 by suitable means such as a set screw 83. For reasons hereinafter explained, the cam member 81 is formed in such a manner so that approximately 45 degrees of the 360 degrees of travel is used for the return and 315 degrees of the 360 degree of travel is utilized for delivery. The cam member 81 is adapted to engage a roller 84 which is disposed in a slot 86 at the rear extremity of the piston member 71 and which extends in a direction which is parallel to the axis of the piston member. The roller 84 is mounted upon a pin 87 mounted in the piston member and extending through the slot 86. As can be seen, the cam member 81 is of a width so that it can extend into the slot 86 in the piston member 71 and engage the roller 84.

The shaft 82 carrying the cam member 81 is rotatably mounted in bearings 88 mounted in the plates 57 and 58. Means is provided for rotating the shaft 82 and consists of a spur gear 89 mounted on the shaft 82 which is driven by a pinion gear 91. The pinion gear 91 is driven by a stepping motor 92 of a conventional type which is mounted on a plate 93 supported by posts 94 and screws 96 on the rear plate 58. A vane 97 is carried by the shaft 82 and rotates with the shaft 82 and is diposed between the gear 89 and the plate 53. The position of the vane 97 is adapted to be sensed by a sensor assembly 98 mounted on the plate 93.

A cylindrical fitting 101 is provided which extends through a bore 102 provided in the plate 58 and this is provided with a threaded boss 103 that is threaded into the body 59. The fitting 101 is provided with a bore 104 which opens into the bore 62 in the body 59. A pressure transducer 106 of a suitable type such as a Microswitch No. 136 PC 15 GI is mounted in the fitting 101. An O-ring 107 is provided for establishing a good seal between the fitting 101 and the pressure transducer 106.

A circular sleeve 111 is mounted in the bore 63 in the plate 57 and opens into the cylindrical recess 62. The sleeve 111 is formed of a suitable material such as brass and is mounted in the body 59 so as to form a liquid type seal between the sleeve and the body. A circular rubber diaphragm 112 is bonded to the outer extremity of the sleeve 111 in a suitable manner such as by vulcanizing. From the construction shown, it can be seen that the interior of the sleeve 111, the interior of the recess 62, and the bore 67 all form a part of a chamber 114 which is filled with a suitable liquid 116 such as a silicon oil.

The filter and pump assembly 46 is constructed in a manner as hereinafter described and is mounted upon the sleeve 111. It is clamped into the desired position onto the sleeve 111 by a manually operated clamp assembly 121 which is adapted to engage the filter and pump assembly 46 to retain the same in place. The clamp assembly 121 consists of a handle 122 which serves as a clamp which is secured by a screw 123 to a shaft 124 which extends into the handle 122. The shaft 124 extends through a sleeve bearing 126. Suitable means is provided for ensuring that the shaft 124 will rotate with the handle 122 and consists of a pin-and-slot connection in which a pin 127 mounted on shaft 124 seats in slots 128 in the handle 122. The handle or clamp 122 is provided with a nose portion 122a which is utilized for a purpose hereinafter described. A spacer 129 is mounted on the sleeve 126 and a washer 130 is mounted on the shaft 125. A vane 131 is carried by a collar 132 secured to the shaft 124 by a pin 133. The vane 131 rotates with the shaft 126 and is adapted to cause operation of a photoelectric sensor 134 which is carried by the rear plate 58.

Means is provided for ensuring that the handle or clamp 122 will be rapidly moved from an over-center position and consists of a spring 136 that is carried by a pin 137 and which has one end engaging a pin 138 mounted on the plate 58 and has the other hand engaging another pin 139 carried by the handle or clamp 122.

Means is provided for filling the chamber 114 with the silicon oil 116 and consists of the pore 141 which is provided in the body 59 and extends into the bore 62. An adjustable piston 142 is mounted in the bore 141 by threading it into the body 59. The piston 142 is provided with a hexagonal head 143 disposed in a recess 144 provided in the body 159. The adjustable piston 142 is provided with a bore 145 extending axially through same. A plug 146 is threaded into the hexagonal head 143 of the piston 142 to close the bore 145. An O-ring 147 is carried by the innermost end of the piston 142 and engages the side wall forming the bore 141. Initially, the chamber 114 is filled with the liquid 116 with the plug 146 removed. In order to eliminate any possible air bubbles from the liquid 116, the mechanical drive assembly 56 is placed in a vacuum to permit the air in the liquid to escape therefrom. Thereafter, the plug 146 is inserted and then the piston 142 is adjusted so that the diaphragm 112 is slightly convex or alternatively substantially planar.

The construction of the filter and pump assembly 46 may now be described. It consists of first and second parts 161 and 162 formed of a suitable material such as plastic. Part 161 is formed with an inlet fitting 163 which is with an inlet port 164. Part 162 is provided with an outlet fitting 166 and an outlet port 167 therein. The parts 161 and 162 are formed of a suitable low cost material such as plastic so that they can be joined together by suitable means such as ultrasonic bonding. When joined, the parts 161 and 162 form a chamber or space 168 therebetween which is in communication with the inlet port 164 and the outlet port 167. The part 162 is provided with a centrally-disposed bore 169 which also is in communication with the chamber 168.

Means is provided for minimizing the space within the chamber 168 that can be occupied by the IV liquid and consists of a filter support plate 171 formed of a suitable material such as plastic which is disposed in the chamber 168 between the parts 161 and 162. The plate 171 can be generally circular in configuration and is provided with an inner circular recess 172. A space in the form of slot 73 is provided in the filter support plate 171 extending diametrically of the same within the circular recess 172 and opens through both sides of the filter support plate 171. The space 173 is formed by arcuate walls 174. A bore 176 is formed in the filter support plate 171 and is generally in alignment with the outlet port 167. The filter support plate 171 is provided with an annular outwardly extending projection 177 which serves as a valve seat adapted to be engaged by a valve member 178. The valve member 178 as shown is a part of the circular member 179 formed of a suitable material such as rubber which is disposed between the filter support plate 171 and the interior of the part 162 so as to form a diaphragm which overlies the large bore 169 and covers the same and which also serves to provide the valve member 178 as a part thereof. The circular diaphragm member 179 is provided with a plurality of holes, as for example four holes 181, which surround the circular valve member 178 forming a part of the circular member 179.

Figure 7:
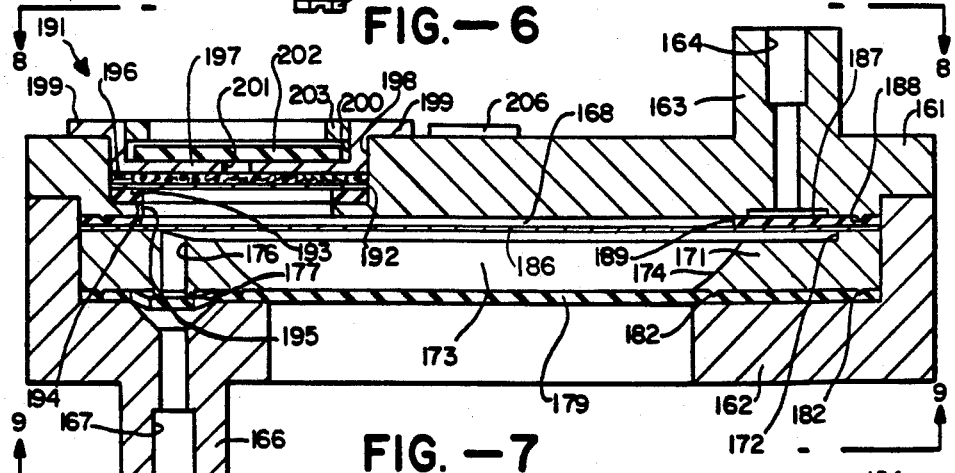
FIG. 7 is a cross-sectional view taken along the line of 7—7 of FIG. 1 showing in particular the combination filter and pump assembly.
Figure 7B:
FIGS. 7A and 7B are detail views of the inlet and outlet valve assemblies shown in FIG. 7 showing the same in open positions.

As can be seen, when the circular valve member portion 178 of the diaphragm 179 is depressed away from the valve seat 177 as shown in FIG. 7b, liquid can flow through the bore 176 and through the holes 181 through the outlet port 167. The filter support plate 171 is also provided with annular energy directors 182 which engages the resilient circular member 179 to form a liquid tight seal between the filter support plate 171, the circular diaphragm member 179 and the part 162.

A circular hydrophilic filter 186 is disposed over the filter support plate 171 and divides the chamber 168 into first and second regions in which the first region is in communication with the inlet port 164 and the second region is in communication with the outlet port. As is well known to those skilled in the art, a hydrophilic filter is of the type which when wetted will resist the passage of air through the same and before wetting will permit the passage of air through the same. A gasket, 187 (see FIG. 10) formed of a suitable member such as rubber overlies the filter member 186 and is clamped between the part 161 and the filter support plate 171. An annular energy director 188 is carried by the part 161 and serves to form a good seal between the gasket 187 and the part 161 as well as with the filter support plate 171. The gasket 187 is provided with a D-shaped opening 189 which overlies the space 173 in the support plate 171.

A hydrophobic filter assembly 191 is mounted in the part 161 in a position which is spaced from the inlet fitting 163 and which is generally in alignment with the outlet fitting 166. It preferably should be located adjacent the uppermost portion of the chamber 168 when the filter and pump assembly is disposed in a generally vertical position as when in use as shown in FIG. 2. The hydrophobic filter assembly 191 consists of a hydrophobic filter member or membrane 192 of a conventional type. The outer annular margin of the membrane is engaged by a rubber seal ring 193 carried by an annular shoulder 194 formed in the member 161. The shoulder 194 defines a large opening 195, in the part 161 which opens into the chamber 168. A circular member 196 porous to air overlies the membrane 192 and is formed of a suitable material such as a fiber polyester which alternatively can be formed as a part of the filter itself. A circular cap 197 is seated in a circular recess 198, formed in the part 161 and overlies the member 196 to clamp the outer annular lip 199 which overlies the part 161. The cap 197 is provided with an annular lip 199 which overlies the part 161. The cap 197 is provided with a large circular recess 200 which is in communication with a hole 201 opening into the member 196. A one-way valve member in the form of a rubber disc 202 overlies the hole 201 and is carried by the cap 197. A retaining ring 203 is mounted in the recess 200 of the cap 197 and serves to retain the outer margin of the one-way valve member 202 for movement between open and closed positions with respect to the hole 201.

A semicircular stop 206 is carried by the part 161 and is adapted to be engaged by the nose 122a of the handle or clamp 122.

The electrical circuitry which is utilized for operating the controller 21 is shown in block diagram form in FIG. 13 and is mounted behind the panel 51. This electrical circuitry includes an alpha-numeric display panel 211 provided in the front panel 51. The alpha-numeric display 211 can be of any suitable type as for example a liquid crystal display which displays message outputs and warnings such as "infiltration", "excess pressure", "empty bottle", etc. This display 211 also serves as an entry register for numbers entered on a keyboard 212 which will be visible until the destination is specified by the appropriate key in the keyboard. The functions given individual keys 213 of the keyboard 212 are shown in FIG. 1 and includes "START", "STOP", "PRIME", "SENSITIVITY", "RATE", and "TOTAL". The keyboard 211 is constructed in a suitable manner but preferably is a keyboard which provides a smooth surface which would be unaffected by spillage of liquid. The keyboard is of a type in which individual keys 212 are actuated by being contacted by a finger or a human hand. Additional displays 216, 217, 218 and 219 have been provided with displays 216, 217 and 218 being four-digit displays and display 219 being a two-digit display. Display 216 shows the amount of milliliters remaining to be delivered whereas display 217 shows the amount of milliliters already delivered to the patient. Display 218 shows the rate of delivery in milliliters per hour. Display 14 is a two-digit display of the alarm sensitivity in percent above the memorized benchmark pressure which is ascertained in the manner hereinafter described. These displays 216, 217, 218 and 219 can be liquid crystal type displays.

Status lights 221, 222 and 223 are provided in the front panel 51 and show normal, warning and alarm conditions by green, yellow and red light emitting diodes respectively.

All three lights are off when the pump is not operating. An on/off power switch 226 is also mounted on the front panel 51 and an indicating light 227 is provided to indicate when the power is on. An opening 228 is provided in the front panel 251 and is covered with a material 229 which is generally impervious to liquid but which are disposed behind the material 229 to provide warning and alarm tones.

In FIG. 13 there is shown a block diagram of a microprocessor which can be utilized in connection with the controls provided on the panel 51 of the controller 21. The microprocessor can be of any suitable type of processor such as an 80 or 16-bit type as for example type o processor such as an 8- or 16-bit type as for example the R6502 manufactured by Rockwell International Corporation of Anaheim, Calif. Such a microprocessor includes a clock generator 236 of a conventional type which supplies its signal to the microprocessor 237. The microprocessor 237 is connected to a 16-bit address bus 238 and an 8-bit data bus 239. Typically, the address bus 238 is unidirectional whereas the data bus 239 is bidirectional. Both buses are connected to a read only memory (ROM) such as one or more R2332s supplied by Rockwell International. Alternatively, programmable ROM (PROM) devices may be used. A random access memory (RAM) consisting of two or more R2114 circuits supplied by Rockwell International may also be used and connected to the data bus and address buses 238 and 239. The decoder 243 is of a conventional type and is connected to the address bus 238 and serves the function of individually enabling via select lines the memory or the I/O addressed by the microprocessor 237. A plurality of I/O ports 246-249 and 251-253 are provided which are connected to the data bus 239, which ports are utilized for interfacing with the user and other parts of the controller. The R6522 integrated circuit contains two such 8-bit I/O ports. The dual I/O 248 requires both ports of an R6522 integrated circuit. The I/O 256 supplies information to a motor drive circuit 261 which is of a conventional type for driving the stepping motor 92 which in turn drives the filter and pump assembly 46 in the manner hereinafter described. The motor drive 261 will cause the stepping motor 92 to start, stop and run at varying speeds. During the first 45 degrees of travel of the cam member 81, representing the filling phase, the angular velocity will be substantially constant whereas during the remaining 315 degrees of travel representing the delivery phase, a variable speed of rotation is utilized. Pressure is sensed by the pressure transducer 106 and its signal is supplied through an operational amplifier 262 which supplies its information to an analog to digital converter 263. The digital signal provided by the analog to digital converter 263 is read by the microprocessor 237 and supplied to the I/O port 254.

The angular position and RPM of the stepping motor 92 is read by the position transducer 98. The position transducer 98 can be of any suitable magnetic optical type as for example a model FPA103 manufactured by Fairchild Semiconductor Corporation of Mountain View, Calif. The signal supplied by the transducer 98 is supplied through a Schmitt trigger circuit 267 to the I/O port 256 will sense a transition when the stepping motor 92 is passing through its zero degree position.

The I/O ports on 246-249 and 251-253 are coupled to the front panel displays as shown in FIG. 13. Operation of the IV system with the controller 21 and the combination IV filter and pump assembly 46 utilizing the method of the present invention may now be briefly described as follows. Let it be assumed that it is desired to administer an IV solution to a patient utilizing the system hereinbefore described. A suitable container of IV solution such as the bottle 28 is selected and the needle 36 of a drip chamber 34 is inserted through the stopper 32 carried by the bottle. The tube 38 is connected to a conventional drip chamber 34 of the vented or unvented types and an on/off clamp 39 is provided on the tube 38. The bottle 28 is suspended at an elevation which is several feet above the filter and pump assembly 46 to fill the filter and pump assembly 46. This can be accomplished by suspending the bottle 28 from the hanger 27 carried by the pole 24. As soon as the on/off clamp 39 is moved to the "on" position, liquid will flow out of the bottle 28 through the tube 38 and into the filter and pump assembly 46. It is important in filling the filter and pump assembly 46 that the assembly 46 be disposed in such a position so that the hydrophobic vent filter is in an uppermost position with respect to the chamber in the filter and pump assembly 46. It can be held in this position by hand, or alternatively, it can be placed in the controller by inserting the filter and pump assembly sideways into the controller so that the outlet 47 extends into the slot 53 provided in the controller and so that the tube 48 extends outwardly from the slot 53. When the filter and pump assembly is properly positioned, the clamp or handle 22 can be rotated counterclockwise as viewed in FIG. 1 until the nose 122a swings into a center position and comes into engagement with the stop 206. At the same time that this is occurring, the vane 131 will be moved into a position where it overlies the sensor 134 to give an indication to the electrical circuitry that the filter and pump assembly 46 is properly positioned on the controller 21.

Figure 7A:
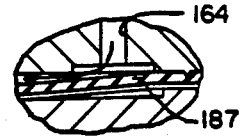

During the filling operation, liquid from the bottle 28 enters the inlet port 164. The force of gravity on the IV liquid from the elevated bottle 28 causes the gasket 187 which serves as a valve member to be moved into an open position as shown in FIG. 7A to permit liquid to pass into the chamber 168 and into the region disposed on one side of the hydrophilic member or membrane 186. The liquid will pass through the hydrophilic membrane and thus liquid will gradually fill the regions on both sides of the filter 186. As the liquid rises it moves any air in the regions on opposite sides of the filter member 186 upwardly. Since the upper portion of the membrane is still unvented air can pass through the hydrophilic filter to be vented to ambient through the hydrophobic filter 192 to ambient. In this all air in the space 168 and the regions on opposite sides of the hydrophilic filter is vented to ambient through the hydrophilic filter 192. As soon as the filter and pump assembly 46 is substantially filled, the liquid will enter the opening 195 and come into contact with the hydrophobic filter 192 which as is well known to those skilled in the art is of a type which will not absorb a liquid but which will let air pass therethrough. Any air in the chamber 168 and in the region on the inlet side of the hydrophilic membrane 186 and passing through the hydrophobic filter will pass through the hole 201 and will move the one-way valve member 202 away from the hole 201 and pass around the one-way valve 202 to ambient.

In operating the controller 21, the operator first turns the power on/off switch 226 to the "on" position. The operator after the initial filling the filter and pump assembly or cassette 46 then pushes the "prime" key button 213 of the controller to remove air from the distal tube of the filter and pump assembly 46. Next the operator pushes the total milliliters pushbutton, the rate of milliliters per hour, and the sensitivity percent button and these numbers will be entered in the appropriate memory register of the microprocessor and also will transfer to a corresponding display.

If the sensitivity key is actuated without any number in the entry register, the operator can measure pressure changes due to movement such as raising and lowering the arm of the patient. The maximum percent change thus produced will be displayed and the operator may leave it as an alarm threshold or change it by keyboard entry. The start key will not only initiate the pumping action but will also cause the pressure to be measured, averaged and memorized as a benchmark for use during the first few second of operation. Thereafter this value will be used in calculating the pressure changes and selecting the corresponding message displays, warning and alarm signals. The stop key interrupts the pumping but does not change any of the settings. The operator may restart or change any of the parameters as desired utilizing the keyboard. Additional keys can be ordered and programmed to serve special functions such as the decimal point for fractional numbers, "standby" (very low rate), operation or "omit" to signal that a given parameter is intentionally not set. The keyboard preferably is a matrix scanned type of keyboard.

If desired, a more elaborate dialogue can be had with the operator or the controller. If the apparatus is programmed to ask questions, such as "unlimited total" the value to be delivered is unspecified. If that is the operator's intention, the operator will answer "yes" and if this was an oversight of the operator, the answer will be "no." The processor will then ask for the total milliliters which can be keyed in by the operator. When delivery of the predetermined amount of liquid is complete, the pumping rate can be changed by the microprocessor to a standby needle keep-open rate.

In commencing operations, the microprocessor 237 can be operated as follows. As soon as the power is turned on, the microprocessor will then perform a number of self-tests of the appropriate type desired. For example, on both memories, most of the I/O ports, readouts, the motor drive, the motor pressure and position transducers can be checked by the microprocessor. As soon as this has been done, the microprocessor may display "ready" on the display 211. Alternatively, if there is a difficulty it can state that "service needed". The microprocessor 237 reads instructions from the ROM memory 242 and performs internal functions or reads or writes using the RAM memory 241 or the I/O port hereinbefore described. In connection with this programming, the microprocessor 237 may display an operator code message so that an authorized user can be identified by a numerical code. As can be appreciated, the microprocessor can recognize numerous computer terminal codes. This is desirable to prevent incorrect, such as accidental, curious or malicious, keyboard operation as for example by visitors to a hospital ward. Such an attempt may be made to cause an alarm. The microprocessor 237 may also be programmed to memorize and recall the code numbers of previous operators. The operator may enter the desired data or the apparatus may display prompting messages such as "total ML?" or "rate ML per hour?" for the user to answer.

When the controller 21 is turned on by operating the power switch 226 and operating the "start" button, power is supplied to the motor drive 261 to drive the stepping motor 92. Operation of the stepping motor 92 causes rotation of the pinion gear 91 which rotates the gear 89 to drive the cam member 81. Driving of the cam member 81 causes a reciprocatory movement of the piston member 71 against the force of the return spring 92. As the piston is advanced to its forward position as viewed in FIG. 3, liquid within the bore 67 will be forced outwardly into the chamber 114 through the slots 79 carried by the piston member 71. As the liquid is pushed out, the diaphragm 112 will bulge outwardly to provide additional space to accommodate the liquid pushed out of the bore 67 by the forwardly moving piston member 71 so that it will assume a convex or a more convex position depending upon the initial position of the diaphragm 112. As this is occurring, the diaphragm 112 is in intimate engagement with the diaphragm 179 of the filter and pump assembly 46 so that it is caused to assume a concave position. As this is occurring, increased pressure is applied to the liquid within the chamber 168 and within the space 173 to cause the liquid to be moved under pressure through the bore 176 to move the portion of the diaphragm 179 overlying the bore 176 to cause the valve member to move away as shown in FIG. 7B to permit liquid to pass through the holes 181 through the outlet port 167 and thence into the outlet tube 48 and through the needle 49. As the cam 81 continues to rotate, the cam permits the piston member 71 to return to its retracted position under the force of the return spring 72 which causes liquid within the chamber 112 to pass through the slots 79 in the opposite direction and into the bore 67 and at the same time relieving pressure on the diaphragm 112 so that it returns to its normal or initial position and brings with it the diaphragm 179. As the diaphragm 179 returns from a concave position to a planar position and to a convex position, a reduced pressure will be created within the chamber 168 to cause the inlet valve formed by the gasket 187 to open as shown in FIG. 7A to again permit additional liquid to drain from the bottle 28. This additional liquid will pass through the hydrophilic filter 186 and through the outlet valve means as hereinbefore described. As soon as sufficient liquid has been pumped by the filter and pump assembly 46 to cause the liquid to be discharged from the needle 49, the system is primed and completely filled with liquid. The needle is then introduced into the vein of the patient to commence intravenous feeding.

Let it be assumed that the control panel 51 has been set up in the manner hereinbefore explained after the operating perameters for the controller have been defined and inserting through the keyboard 212. The start button may be activated and the pressure benchmark level established. For example, pressure during a pre-programmed number of revolutions may be measured by the microprocessor and stored for later reference. A preset percent increase above the established benchmark level initiates a warning and the "infiltration" message indicating probably a needle has slipped from the blood vessel into adjacent tissue area. If the pressure increase is higher than the user established sensitivity percentage, a computationally derived value provided by the microprocessor 237 related to the pressure of the liquid to be delivered, then an alarm is initiated. For example, this can occur when the needle becomes clogged or the flow is obstructed in some other way such as by a sharp bend in one of the IV tubes. If the pressure decreases below the benchmark level is lower by more than the user established sensitivity percentage, an alarm is also inititated. This may be due to a broken tube, an empty bottle, air in the cassette, etc. Each of these would generate an alarm. Various diagnostic displays can be provided if desired.

If a change is desired after the controller has been purchased of a particular ROM or PROM chip in the controller 21, it can be changed merely by exchanging the ROM and PROM chip or by reprogramming. The microprocessor 37 can be utilized to monitor other operations. For example, it can be continuously check the motor RPM measured by the position sensor against the programmed RPM. It can check battery voltage, etc. and send an alarm if anything fails including itself, the latter being implemented by an alarm being prevented only by a continuously processor-triggered monostable multivibrator. The microprocessor 237 can also be connected to the photoelectric sensor 134 to determine whether or not the filter pump assembly 46 is properly positioned or not so properly positioned to prevent operation of the filter and pump assembly 46 and by giving an appropriate warning in the display 211 as for example "lock cassette". The microprocessor also can be programmed to show other failure conditions in the display 211 such as "motor stopper" or "low battery". In this way it can be seen that numerous safety features can be readily incorporated into the electronic circuitry.

It should be pointed out that the filter and pump assembly 46 with connecting tubing is not a free flow through device because the valving provided within the filter and pump assembly 46 prevents such flow through whether or not the filter and pump assembly is mounted in the controller 21.

By providing the filter support plate 171 within the chamber 168 with the small space 173 therein, the pump chamber contains a very small amount of liquid as for example less than one cc. for liquid. This is of great advantage when it is desired to switch from one liquid to another which makes it unnecessary for a large bolus of liquid to be introduced into the patient of the previous liquid before the new one can be introduced. This is particularly important with respect to neonatal patients where small quantities of drugs at low rates are to be administered and when rates are changed and are to be supplied to the patient very quickly.

The filter and pump assembly 46 is particularly novel in that it is made substantially entirely of relatively flat parts particularly with respect to the diaphragms, filters and the like. This design particularly lends itself to the inexpensive die stamping of flat parts from sheet material.

The construction of the filter and pump assembly is such that any air passing from the bottle and into the tube and into the filter and pump assembly 46 can readily exit through the hydrophobic filter assembly 191 while at the same time utilizing the same body containing the pump for carrying hydrophilic filter for preventing air reaching the outlet of the filter and pump assembly 46. It should be pointed out that the hydrophilic filter provides a bacteric eliminating feature which is very advantageous. However, if desired it can be omitted and the filter and pump assembly will still operate without letting air pass through the assembly 46. Air will not pass through the assembly 46 because the hydrophobic filter 192 vents at a pressure less than the pressure required to open the outlet valve member 178.

The controller 21 itself is of a unique construction in that it utilizes a microprocessor for controlling its functions. In addition, it has a number of very advantageous mechanical features. For example, the piston member 91 which is guided in both its front and rear extremities so large precision tearing surfaces are provided to minimize any wear on the piston and to thereby retain precision pumping accuracy. Because of the manner in which the piston member is moved between its forward and retracted positions, there is no backlash and therefore it pumps with great accuracy.

As pointed out previously, any surface which is engaged by the sealing O-ring 76 is not utilized for forming a bearing engagement between the piston-like member 71 and the bore 66 and 67 in which is travels.

It will be noted that the cam member 81 is constructed in such a manner so as to give the longest length of time possible for supplying the liquid to the patient while using a relatively small portion of each 360 degrees of cam travel for the return of the piston-like member 71 to its retracted position. The program for the microprocessor 237 is set so that as soon as the highest point is reached, and the return is started, the stepping motor is speeded up to accomplish the return as rapidly as possible. Only a single photo cell is required for ascertaining when the top of the cam travel is reached in each 360 degrees. This position is sensed by the sensor assembly 98 when the vane 97 moves over the same.

From the foregoing it can be seen that there has been provided a controller and a filter and pump assembly which are relatively simple in construction and which can be readily fabricated. All the filtering is provided in the pump itself for filtering out bacteria prior to at least the last pressure valve in the pump assembly. A hydrophobic filter vents small amounts of air entering the pump assembly. A hydrophilic filter prevents air from being supplied to the patient. In addition, particulates cannot reach the patient. Alarms can be readily initiated without the necessity of sensing a vacuum because pressure sensing is utilized at all times and is capable of initiating alarms for overpressure and underpressure conditions. For example, when air enters into the chamber 168 and an attempt is made to pump this air, a lesser pressure above ambient and below a predetermined level or bench mark pressure will be created because the air vented to ambient under less pressure than that required for opening the outlet valve 178 through the hydrophobic filter 192. This decrease in pressure can be sensed to turn off the pump motor. Similarly, if there is blockage in the needle, a positive pressure above ambient and above a predetermined level or bench mark pressure will be created within the chamber 168 which can be sensed to actuate the alarm. In this way, it can be seen that the filter and pump assembly 46 is particularly safe for a patient both from a bacterial standpoint and from an air standpoint. The filter and pump assembly is particularly advantageous in that it eliminates small quantities of air automatically.

From the foregoing, it can be seen that there has been provided a greatly improved filter and pump assembly and a controller and system for driving the same having numerous advantages.

Figure 14:
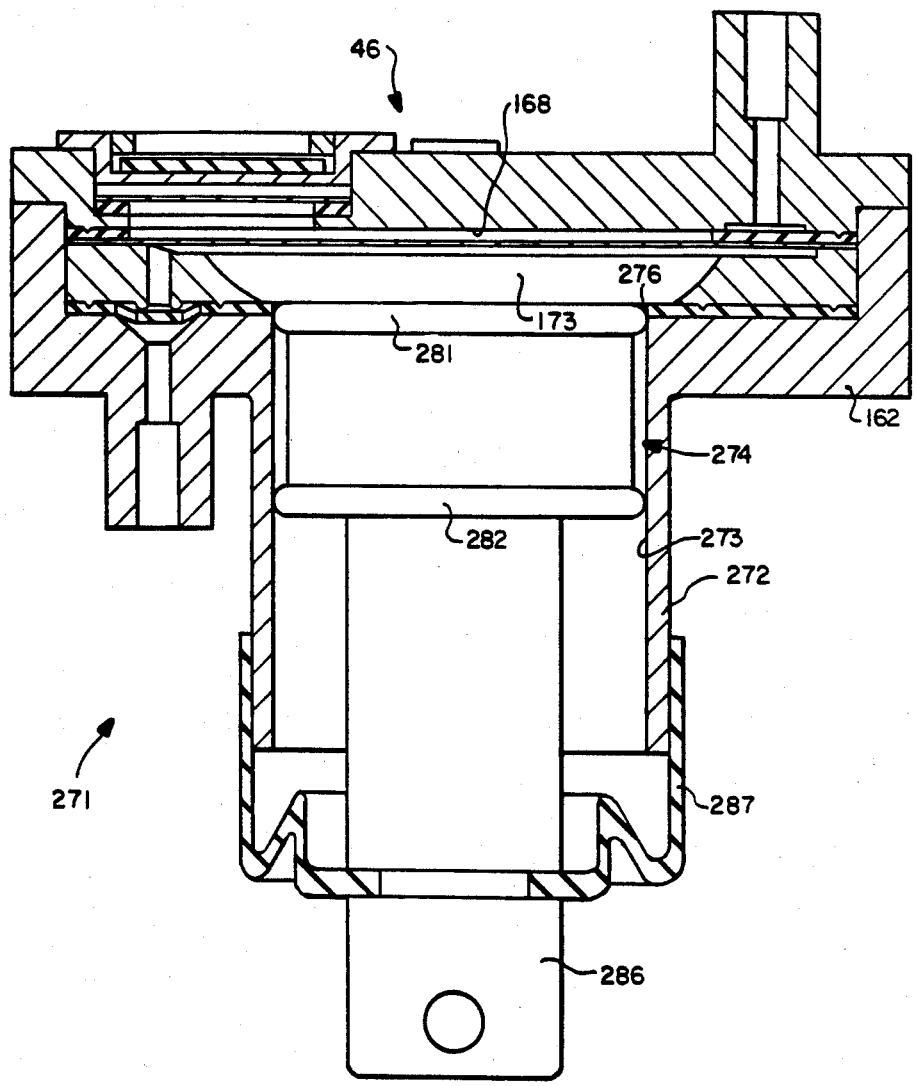
FIG. 14 is a cross-sectional view of another embodiment of the combination filter and pump assembly incorporating the present invention.

In FIG. 14 there is disclosed another mechanical drive assembly 271 for operating a filter and pump assembly 46 of the type hereinbefore described. The filter and pump assembly is substantially identical to the one hereinbefore described with the exception that the part 162 is provided with a cylindrical extension 272 which has an interior cylindrical surface 273 which serves as a cylinder 273. A piston assembly 274 is mounted in the cylinder 273 and is adapted to be moved between retracted and forward positions. The diaphragm 179 has been provided with a central opening 276 through which the piston 274 is adapted to extend. The interior of the cylinder 273 is in communication with the slot 173 and with the chamber 168. The piston member 279 is of a diameter slightly less than the cylinder 274 but is provided with spaced apart O-rings 281 and 282 which engage the sidewalls of the cylinder 273 and form a sealing engagement between the piston member 274 and the sidewalls of the cylinder 273. The piston member 274 is provided with a piston rod 286 which is adapted to be connected to suitable driving means such as an eccentric (not shown) driven by the stepping motor 92. A rubber boot 287 is mounted on the piston rod 286 near the outer extremity of the same and forms a sealing engagement with the cylindrical extension 272.

Operation of this embodiment of the controller is substantially indentical to that hereinbefore described with the exception that the reciprocation of the piston rod 286 causes movement of the piston 274 to cause operation of the valve members shown in FIGS. 7A and 7B to cause fluid to be pumped from the inlet to the outlet in the manner hereinbefore described, the movement of the piston taking the place of movement of the diaphragm 179 in the first described embodiment.

In FIGS. 15 and 16 there is shown another embodiment of an IV system 301 of the present invention. It consists of a controller 302 which is mounted in a cabinet 303. The cabinet 303 is mounted on a post 24 in much the same way that the cabinet 22 of the controller 21 shown in FIGS. 1 and 2 was mounted. It is provided with first and second front panels 304 and 306 with the front panel 304 being disposed above the front panel 306.

The controller 302 includes a pump drive module 308 which drives a cassette or pump 311 which is removably mounted there on by the use of a tool clamp assembly 312.

Figure 17:
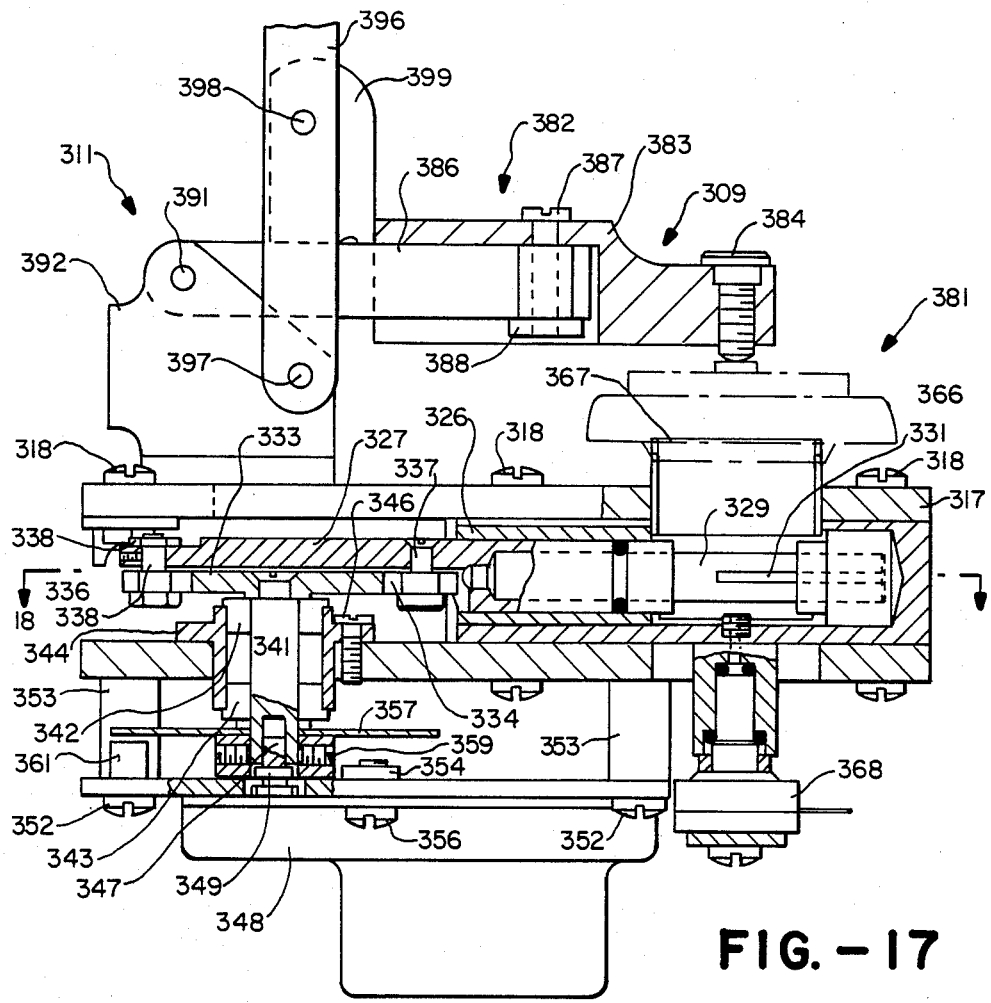
FIG. 17 is an enlarged view, partially in cross section of the drive module for the cassette in the controller as shown in FIGS. 14 and 15.
Figure 18:
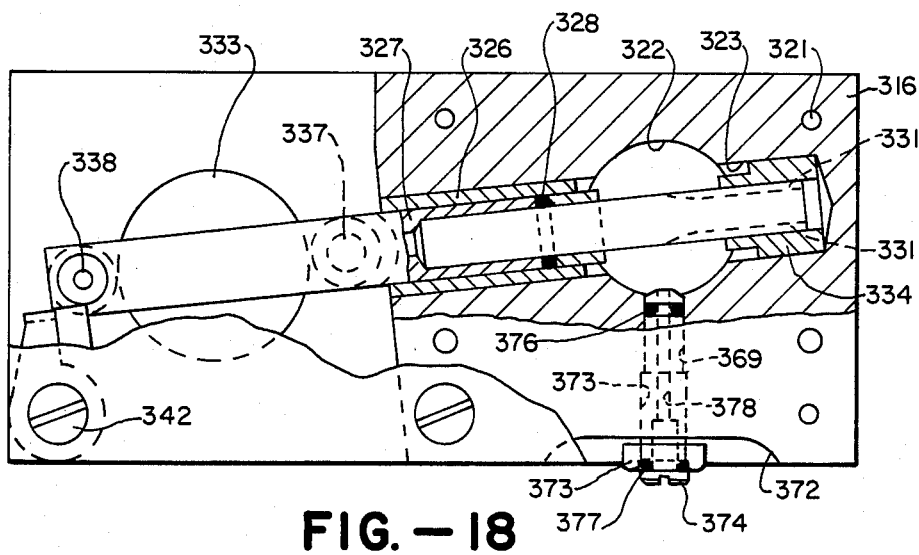
FIG. 18 is a partial cross-sectional view taken along the line 18—18 of FIG. 17.

The pump drive module 309 is shown in detail in FIGS. 17 and 18 and as shown therein consists of a cylinder block 316 which has a face plate 317 secured thereto by suitable means such as screws 318 and a rear plate 319 secured thereto by suitable means such as screws 321. The block 316 is provided with a hole 322 which extends therethrough. A cylindrical bore or recess 323 extends into the cylinder block 316 in a direction which is at right angles to the hole 322 and extends through the hole 322 at an angle with respect to the sides of the cylinder block 316. A piston rod bearing 324 is seated in the extreme end of the cylindrical recess 323. A cylinder sleeve 326 is mounted in the other end of the cylindrical recess or bore 323 and has disposed therein a support sleeve 327 which carries an O-ring 328. A piston rod 329 is slidably mounted in the support sleeve 327 and is adapted to extend into the piston rod bearing 324. The piston rod 329 on its distal end is provided with two slots 331 spaced 180° apart which extend longitudinally of the piston rod 329 from approximately the mid point of the piston rod to the distal extremity of the same and open through the sides of the piston rod.

The cylinder sleeve 326 which carries the piston rod 329 is reciprocated by a cam 333 which is adapted to engage bearing assemblies 334 and 336 rotatably mounted on a bearing stud 337 and mounted on an eccentric stroke adjustable stud 338, both of which are carried by the support sleeve 327. The cam 333 is driven by a cam shaft 341 rotatably mounted in upper and lower bearings 342 and 343 carried by a flanged bearing block 344. The flanged bearing block 344 is secured to the rear plate 319 by screws 346. The cam shaft 341 is driven by an output shaft 347 of a motor 348 and is connected thereto by suitable means such as a pin 349. The motor 348 is mounted upon a PC board 351 which is secured to the rear plate 319 by the use of screws 352 extending through spacers 353. The motor 348 is secured to the PC board 351 by screws 354 threaded into nuts 356.

Timing means provided for controlling the operation of the piston rod 329 includes a timing disc 357 mounted upon a hub 358. The hub 358 is secured to the cam shaft 341 by set screws 359. A photosensor 361 is mounted upon the PC board 351 and is provided for sensing the various positions of the timing disc 357.

A support tube 366 is mounted in the face plate 317 and is in communication with the hole 322 in the cylinder block 316. The support tube 366 is cylindrical and extends outwardly from the face plate 317 in a direction at right angles to the surface of the face plate. The outer extremity of the support tube is enclosed by a flexible membrane 367 which extends over the same and is bonded to the outer extremity of the same to form a liquid-tight seal.

A microswitch pressure sensor 368 of a conventional type is mounted in the rear plate 319. The sensor 368 is in communication with a bore 369 which is in communication with the hole 322 provided in the cylinder block 316.

The cylinder body 316 is also provided with a threaded bore 371 which extends from a recess 372 on one side of the cylinder block and extends into the hole 322. A screw assembly 372 is provided which consists of an outer screw 373 and an inner screw 374. The inner screw 374 is threaded into the outer screw 373. The outer screw 373 is threaded into the bore 371 and carries an O-ring 376. Another O-ring 377 is provided which forms a seal between the screw 374 and the screw 373. The screw 373 has a flow passage 378 extending therethrough which upon removal of the screw 374 permits air to be exhausted from the hole 322 and also permits filling of the hole 322 with a suitable liquid. After the hole 322 has been filled, the outer screw 373 can be adjusted to move it inwardly and outwardly to thereby control the shape of the membrane 367 carried by the support tube 366.

A cassette-type pump 381, the details of which will be hereinafter described, is mounted upon the support tube 366 and is held in place by a clamping assembly 382. The clamping assembly 382 is of a conventional toolclamp type. The clamping assembly 382 consists of a clamping member 388 which carries an adjustable pin 384 which is adapted to engage the cassette 381. The clamping member 386 is carried by an arm 386 which is secured to the clamping member 383 by a screw 387 threaded into a retaining member 388. The arm 386 is pivotally mounted on a pin 391 carried between a pair of spaced apart ears 392 mounted upon the face plate 317. A handle 396 is provided for operating the arm 386. The handle 396 is pivotally mounted on a pin 397 also mounted between the ears 392. The handle 396 is also pivotally connected by a pin 398 to an arm 399. The handle 396 carries a knob 401 which is adapted to be grasped by the hand to facilitate moving the clamping assembly 382 between the cassette clamping and cassette unlocked positions permitting insertion and removal of the cassette 381.

The detailed construction of the cassette or filter and pump assembly 381 is shown in FIGS. 19, 20 and 21. As shown therein, the cassette 381 consists of three parts 406, 407, and 408 formed of a suitable material such as plastic. The part 406 which also can be called a top cover is formed with an inlet fitting 409 which is provided with an inlet passage or port 411. Part 408 which also can be called a bottom cover is provided with an outlet fitting 412 which has an outlet passage or port 413 therein. The part 406 is provided with a recess 414 which is adapted to receive the intermediate part 407 which also can be called a distal valve pad. A pair of resilient gasket members 416 and 417 of a suitable material such as rubber are disposed on opposite sides of the part 407 to form liquid-tight seals between the parts. After the resilient members 416 and 417 have been inserted in the manner shown in FIG. 21 in the drawing, the parts 406 and 408 can be bonded together in a suitable member as, for example, by ultrasonic bonding.

The bottom cover or part 408 is provided with a large centrally disposed bore 418 which is adapted to seat over the support tube 366 so that the membrane 367 carried by the support tube comes into intimate contact with the cassette membrane provided by the resilient member 417. When the cassette is in position on the support tube 366, it can be clamped in that position by the use of the clamping assembly 382 in which the pin 384 engages a centrally disposed conical recess 419 provided as a part of the part 406. The recess 419 is disposed in a centrally disposed boss 421 which is supported by radially extending reinforcing ribs 422. The resilient member 416 includes a portion which serves as a valve member 426 which underlies the inlet port 411 and is movable into and out of engagement with a valve seat 427 surrounding the inlet port 411.

A filter element 428 which has an outer perimeter which corresponds with the outer perimeter of the resilient member 416 is provided. The filter element can be of any suitable type such as one manufactured by Gelman Sciences, Inc. of Ann Arbor, Mich. and having a suitable pore size such as 0.020 microns. This filter element 428 is continuous and underlies the valve member 426 as well as substantially the entire remaining portion of the top cover 406. A spherical cavity 429 underlies the valve member 427 and a portion of the filter element 428. The cavity is adapted to receive the valve member 426 when the inlet valve member 426 is moved towards the open position. The intermediate part 407 is provided with a centrally disposed projection or tab 431 which extends through a hole 432 provided in the member 417 and extends into a recess 433 provided in the bottom member 408.

An annular recess 434 provided in the top cover 406 is concentric with the inlet passage 411 and surrounds the valve member seat 427. The recess 434 opens into a recess 436 extending longitudinally of the top cover 406 which overlies the filter element 428. There is also provided a recess 437 in the intermediate part 407 which is in communication with the recess 429 and in communication with the space 438 underlying the filter element 428. A recess 439 which opens into the space 438 establishes communication with the recess 429 provided in the part 407 and immediately underlies the filter element 428. The space 438 between the resilient member 417 and the filter element 428 is in communication with the recess 441 provided in the intermediate part 407. The recess 441 is in communication with a flow passage 442 which extends in a direction substantially at right angles to the general plane of the part 407. The flow passage 442 opens into an annular recess 433 which surrounds a valve seat 444 and which is in communication with an outlet valve member 446 which is formed as a part of the resilient member 417. The valve member 446 is adapted to engage the circular seat 444 and is movable between open and closed engagements with respect thereto. The valve member 446 is provided with a centrally disposed opening 447 extending therethrough through which fluid can pass from the passage 442 past the valve seat 441 and through the opening 447 into the outlet flow passage 443 when the valve member 446 moves to an open position away from the seat 444. When the valve member 446 in the closed position with respect to the seat 444, liquid cannot pass from the passage 447 to the outlet passage 413.

A hydrophobic filter assembly 451 generally overlies the outlet valve member 446 and consists of a cap 452 which is seated within a recess 453 provided in the top cover 406. The cap 452 is provided with a downwardly or inwardly facing spherical surface 454 which has a hydrophobic filter 456 mounted thereupon. The filter 456 can be of a suitable type such as a Gortex membrane filter having a suitable pore size such as 0.02 micrometers on a non-woven polyester film. The filter 456 overlies an opening 457 provided in the top cover 406. A gasket 458 forms a seal between the opening 457 and the outer margin of the filter 456. A flow passage 461 is provided in the cap 452 and extends through the cap to the filter 456. The flow passage 461 is adapted to be closed by a one-way valve member 462 which is disposed in the cap 452 in the upper portion thereof and which is retained in the cap 452 by a retaining ring 463. The one-way valve 462 is in the form of a rubber disc which overlies the flow passage 461 and is movable between open and closed positions with respect to the flow passage 461. By stretching the hydrophobic filter over a relatively hard surface, it is possible to retain the integrity of the filter during the pumping action and at the same time preventing flopping or movement of the filter element. By having the hydrophobic stay in place, the filter does not affect the volume of the pump chamber.

Operation and use of the cassette 381 is very similar to the cassette hereinbefore previously described in conjunction with FIGS. 7, 7A and 7B. The hydrophobic and hydrophilic filters perform the same functions. The spherical surface provided for the hydrophobic filter helps to maintain the integrity of the filter by preventing flapping of the filter and loss of accuracy of the volume in the pump chamber.

Liquid flowing from the inlet 411 under the force of the actuator causes the valve member 426 to be moved away from the seat 427 permitting fluid to flow into the arcuate recess 434 and into the recess 436 after which it passes through the filter element 428 and into the region 438. The liquid then passes through the recess 441 through the passage 442 and causing the outlet valve member 446 to move downwardly away from the seat 444 permitting liquid to flow through the opening 447 into the outlet passage 413.

The controller 302 which is utilized for operating the pump module 308 and the cassette or pump 311 includes an electronic system of the type hereinbefore described in conjunction with the embodiment shown in FIGS. 1 and 2. However, the front panel of the controller 302 has been changed from the front panel 51 shown in FIG. 1 in that various components have been rearranged. Thus there has been provided an alphanumeric display 466 which can display messages on a liquid crystal display. A keyboard 467 has been provided which includes a plurality of keys 468 having the numerals 0 to 9 thereon as well as prime, start, stop, rate set and volume set keys or pushbuttons. In addition there is provided on and off pushbuttons 471 and 472 for controlling the power to the controller. In addition there are provided other liquid crystal displays which include a volume delivery display 473, a rate per second display 474, and volume remaining display 476, as well as a volume per second display 477. There are two set pushbuttons, one a volume set pushbutton 478, and the other a rate set pushbutton 479. After pushbuttons 478 and 479 have been set, the start pushbutton can be operated to start the delivery of the IV fluid at the prescribed rate and/or volume. Delivery can be stopped at any time by pressing the stop button.

Another embodiment of a cassette and/or pump 481 and a pump drive module 482 is shown in FIG. 22. The pump drive module 482 is like the pump drive modules shown and described in FIGS. 17 and 18 and thus will not be described in detail. The cassette or pump 481 is of the type described in U.S. Pat. No. 4,468,222 with the exception that it has been provided with a hydrophobic vent filter 486 which is mounted in the top cover 487 of the cassette 481 between the inlet passage 488 and the outlet passage 489. The hydrophobic filter 486 is constructed in the same manner in which the hydrophobic filter 451 is constructed in FIG. 21. The cassette or pump 481 is provided with an inlet valve member 491 and an outlet valve member 492. The outlet valve member 492 is adapted to be engaged by a spring loaded plunger 493. This spring loaded plunger 493 has a spring 494 calibrated so that it will open when the pressure in the pump chamber 496 exceeds a predetermined pressure as, for example, that corresponding to 5 to 6 feet of water during the pressure delivery cycle. This pressure represents the benchmark pressure hereinbefore referred to. The inlet valve member 491 is engaged by a valve actuator or plunger 497 which carries a spring 498 which urges the inlet valve member towards a closed position. The actuator 497 is engaged by a lever arm 501 of a solenoid 502.

The fill cycle for the cassette 481 can be accomplished without removing the cassette from the pump drive module 482. During the fill cycle, the inlet valve member 491 is held in an open position by operation of the solenoid 502 to operate the lever 501 to pull the spring downwardly from the inlet valve member 491 against the force of the spring 498. The operation of the solenoid is electronically controlled in time by the controller simultaneously with the switching from a delivery cycle to a fill cycle. Thus it can be seen with a cassette of the type shown in FIG. 22 during the fill cycle, the pump chamber 496 is filled with a liquid by the force of gravity acting upon the liquid at a pressure corresponding to approximately 1 to 2 feet of water. In the event any air enters the system at the time of filling or is forced into the system at any time it will automatically be eliminated through the hydrophobic filter 486. Since any air which enters the pump chamber 496 is almost immediately permitted to escape through the hydrophobic filter 486, there is no opportunity for gas to collect within the pressure chamber 496 and therefore the rate of delivery of fluid through the pump chamber should not vary as the pump drive module 482 operates.

It is apparent from the foregoing that there has been provided a cassette which can utilize a hydrophobic filter of the type described in conjunction with the present invention and that the same can be incorporated with the cassettes of the type described in U.S. Pat. No. 4,468,222 and operate very satisfactorily.

It is also apparent from the foregoing that there has been provided a cassette which can be readily manufactured in quantity at a low cost and which can be readily inserted onto and removed from the controller. The cassette can be readily filled without danger of pockets of air being retained within the cassette. The construction of the cassette is such that the opening and closing pressures can be controlled more precisely.

What is claimed is:

1. In an IV filter and pump assembly, first and second parts, means for securing said first and second parts into a unitary assembly, said first and second parts forming a chamber, one of said parts having an opening therein in communication with said chamber, one of said parts having an inlet port therein, the other of said parts having an outlet port therein, said inlet and outlet ports being in communication with said chamber, inlet valve means controlling the flow of liquid through the inlet port, outlet valve means for controlling the flow of liquid through the outlet port, a hydrophilic member disposed in said chamber and dividing said chamber into first and second regions and in which the inlet port is in communication with said first region and the outlet port is in communication with said second region, hydrophobic filter means carried by said unitary assembly and in communication with said first region, said hydrophobic filter means being disposed in the upper portion of said chamber for venting to ambient small quantities of air in said chamber and means for supplying a pumping action for liquid in said chamber so that it causes liquid to be moved out of the chamber through the outlet valve means and to be moved from the inlet valve means into the chamber.

2. As assembly as in claim 1 wherein said hydrophobic filter means includes one-way valve means.

3. An assembly as in claim 1 together with a filter support plate mounted in said chamber for supporting said hydrophilic filter.

4. An assembly as in claim 3 wherein said hydrophilic filter plate has a slot therein.

5. An assembly as in claim 1 wherein said means for supplying a pumping action includes a diaphragm overlying the opening in said body.

6. An assembly as in claim 5 wherein said outlet means includes a part of said diaphragm.

7. An assembly as in claim 1 wherein said means for supplying a pumping action includes a piston member in communication with said opening in said body.

8. In a system for introducing an IV liquid into the veins of a patient, a support member, a controller, means for mounting said controller on said support member, a source of IV liquid, means for mounting said source of IV liquid on said support member at an elevation which is above the elevation of the controller, a combination filter and pump assembly, said filter and pump assembly having a liquid-tight chamber therein, means for removably mounting said filter and pump assembly on said controller so that the chamber has a vertical dimension, an inlet carried by the filter and pump assembly and being in communication with said chamber in a region adjacent the lower extremely of said chamber, means connecting said inlet to said source of liquid, said filter and pump assembly having an outlet in communication with said chamber and being disposed adjacent the upper extremity of said chamber, hydrophilic filter means having a hydrophilic member disposed within the chamber in such a manner so that liquid from the inlet must pass through the hydrophilic member before it can pass through the outlet, inlet valve means for controlling the flow of liquid through the inlet, outlet valve means for controlling the flow of liquid through the outlet, means connected to the outlet adapted to be inserted into the vein of the patient, means carried by the controller for decreasing and then increasing the volume of said chamber so that said inlet valve means and outlet valve means are operated to cause liquid to pass from the liquid container through the inlet valve means through the hydrophilic filter and through the outlet valve means and into the patient, and hydrophobic filter means in communication with said chamber on the inlet side of the hydrophilic member and being disposed in the upper region of said chamber whereby air passing into the chamber cannot pass through the hydrophilic filter but can pass to ambient through the hydrophobic filter means.

9. A system as in claim 9 wherein said hydrophobic filter means includes a one-way valve means for permitting escape from said chamber to ambient.

10. A system as in claim 9 wherein said means for decreasing and increasing the volume of the chamber includes diaphragm means disposed on one side of the chamber and means for causing the movement of said diaphragm.

11. A system as in claim 10 wherein said means for causing movement of said diaphragm includes an additional diaphragm, means forming a liquid-tight chamber on one side of the diaphragm, a piston extending into said liquid-tight chamber for causing said liquid to move said additional diaphragm to cause said firstnamed diaphragm to move into and out of said firstnamed chamber and means for causing reciprocatory movement of said piston.

12. A system as in claim 11 wherein said means for causing reciprocatory movement of said piston includes a cam, a shaft carrying said cam, means for rotating said shaft, a vane carried by said shaft and being rotated with said shaft and means for sensing the position of said vane to control the reciprocatory movement of said piston.

13. A system as in claim 11 wherein said additional diaphragm is exposed to the atmosphere, wherein said first-named diaphragm of the filter and pump assembly is exposed to the atmosphere, said first-named diaphragm being in intimate contact with the additional diaphragm when said filter and pump assembly is mounted on said controller and releasable clamping means carried by the controller for clamping said filter and pump assembly into position so that said first-named and additional diaphragms are in intimate contact with each other.

14. A system as in claim 8 together with means for sensing the pressure of the liquid in said additional chamber and means responsive to the pressure being measured in said chamber for controlling the operation of said system.

15. A system as in claim 13 wherein said releasable means for clamping said filter and pump assembly to the controller includes a shaft indicating the position of said releasable clamping means, a vane carried by the shaft and movable with the shaft and means for sensing the position of said vane to ascertain when the releasable clamping means i in the proper position to prevent operation of the system until said releasable clamping means is in a proper position.

16. In a system for introducing an IV liquid into a vein of a patient, a support member, a controller, means for mounting said controller on said support member, a source of IV liquid, means for mounting said source of IV liquid on said support member at an elevation which is above the elevation of the controller, a combination filter and pump assembly, said filter and pump assembly having a liquid-tight chamber therein, means for removably mounting said filter and pump assembly on said controller so that the chamber has a vertical dimension, an inlet carried by the filter and pump assembly and being in communication with said chamber in a region adjacent the lower extremely of said chamber, means connecting said inlet to said source of liquid, said filter and pump assembly having an outlet in communication with said chamber and being disposed adjacent the upper extremity of said chamber, hydrophilic filter means disposed within the chamber in such a manner so that liquid from the inlet must pass through the hydrophilic filter member before it can pass through the outlet, inlet valve means for controlling the flow of liquid through the inlet, outlet valve means for controlling the flow of liquid through the outlet, means connected to the outlet adapted to be inserted into the vein of the patient, means carried by the controller for decreasing and then increasing the volume of said chamber so that said inlet valve means and outlet valve means are operated to cause liquid to pass from the liquid container through the inlet valve means through the hydrophilic filter through the outlet valve means and into the patient, said controller being provided with a slot extending horizontally thereof, said outlet of said filter and pump assembly extending into said slot.

17. In an IV system, a source of liquid, a pump assembly having a chamber therein, an inlet carried by the pump assembly and having an inlet port in communication with said chamber, an outlet carried by the pump assembly and having an outlet port in communication with said chamber, inlet valve means for controlling the flow of liquid through the inlet port, outlet valve means for controlling the flow of liquid through the outlet port, a controller for causing a pumping action to occur in said chamber whereby liquid is brought in through the inlet port and discharged through the outlet port, means for connecting the inlet port to the source of liquid, means adapted to connect the outlet port to a patient, hydrophilic filter means disposed in said chamber and dividing said chamber into first and second regions in which the first region is in communication with the inlet port and the second region is in communication with the outlet port, hydrophobic filter means carried by the pump assembly in communication with said chamber for venting the air in said chamber to ambient, said hydrophobic filter means being in communication with the first region and pressure sensitive means carried by the pump for continuously monitoring the pressure in said chamber and actuating an alarm when the pressure in said chamber is above a predetermined pressure and when said pressure is below a predetermined pressure.

* * * * *